US 6,797,721 B2

(12) United States Patent
Uckun et al.

(10) Patent No.: US 6,797,721 B2
(45) Date of Patent: Sep. 28, 2004

(54) PHORBOXAZOLE DERIVATIVES FOR TREATING CANCER

(75) Inventors: Fatih M. Uckun, White Bear Lake, MN (US); Rama K. Narla, St. Paul, MN (US); Craig Forsyth, Roseville, MN (US); Chi Sing Lee, Hong Kong (CN); Feryan Ahmed, Albany, NY (US); Russell Drew Cink, Grayslake, IL (US)

(73) Assignees: Parker Hughes Institute, St. Paul, MN (US); Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 10/146,601

(22) Filed: May 14, 2002

(65) Prior Publication Data

US 2003/0125366 A1 Jul. 3, 2003

Related U.S. Application Data

(63) Continuation of application No. PCT/US00/31388, filed on Nov. 15, 2000.
(60) Provisional application No. 60/165,452, filed on Nov. 15, 1999.

(51) Int. Cl.[7] .................... A61K 31/41; A61K 31/42; A61P 35/00; A61P 35/02; A61P 35/04
(52) U.S. Cl. .................. 514/375; 514/374; 514/359; 514/183; 514/885; 540/468; 800/10; 424/9.2; 424/278.1
(58) Field of Search ................. 514/375, 374, 514/359, 183, 885; 540/468; 800/10; 424/9.2, 278.1

(56) References Cited

U.S. PATENT DOCUMENTS 5,919,816 A * 7/1999 Hausheer et al. ........... 514/449

FOREIGN PATENT DOCUMENTS

WO    WO 01/36394 A1    5/2001

OTHER PUBLICATIONS

Ahmed, F. et al., "Convergent Synthesis of the C31–C46 Domain of the Phorboxazole Natural Products," *Tetrahedron Letters*, vol. 39, pp. 183–186 (1998).
Carbonetto, S., "The extracellular matrix of the nervous system," *Trends in NeuroSci.*, pp. 382–387 (Oct. 1984).
Cink, R. et al., "Stereoselective Synthesis of the C3–C17 Bis–Oxane Domain of Phorboxazole A," *J. Org. Chem.*, vol. 62, No. 17, pp. 5672–5673 (Aug. 22, 1997).
Evans, D. et al., "Application of Complex Aldol Reactions to the Total Synthesis of Phorboxazole B," *J. Am. Chem. Soc.*, vol. 122, No. 41, pp. 10033–10046 (Oct. 18, 2000).
Forsyth, C. et al., "Total Synthesis of Phorboxazole A", *J. Am. Chem. Soc.*, vol. 120, No. 22, pp. 5597–5598 (Jun. 10, 1998).
Knorr, R. et al., "New Coupling Reagents in Peptide Chemistry," *Tetrahedron Lett.*, vol. 30, No. 15, pp. 1927–1930 (1989).
Konig, W. et al., "Eine neue Methode zur Synthese von Peptiden: Aktivierung der Carboxylgruppe mit Dicyclohexylcarbodiimid und 3–Hydroxy–4–oxo–3.4–dihydro–1.2.3–benzotriazin," *Chem. Ber.*, vol. 103, No. 7, pp. 2034–2040 (1970).
Molinski, T., "Absolute Configuration of Phorboxazoles A and B from the Marine Sponge, *Phorbas* Sp. 2. C43 and Complete Stereochemistry," *Tetrahedron Letters*, vol. 37, No. 44, pp. 7879–7880 (Sep. 4, 1996).

(List continued on next page.)

*Primary Examiner*—Frederick Krass
*Assistant Examiner*—Clinton Ostrup
(74) *Attorney, Agent, or Firm*—Merchant & Gould P.C.

(57) ABSTRACT

Synthetic Phorboxazole A and derivatives thereof for the treatment of cancer, including inhibition of cancer cell growth, induction of apoptosis, and inhibition of metastises.

11 Claims, 4 Drawing Sheets-

OTHER PUBLICATIONS

Paterson, I. et al., "Towards the Total Synthesis of Phorboxazoles A and B: Stereocontrolled Synthesis of a $C_{20}$–$C_{32}$ Subunit," *Tetrahedron Letters*, vol. 39, pp. 7185–7188 (1998).

Pattenden, G. et al., "Synthetic Studies Towards Phorboxazole A. A Convergent Synthesis of the C31–C46 Polyene Oxane–Hemiacetal Side Chain," *Tetrahedron Letters*, vol. 39, pp. 6099–6102 (1998).

Rutka, J. et al., "The extracellular matrix of the central and peripheral nervous systems: structure and function," *J. Neurosurg.*, vol. 69, No. 2, pp. 155–170 (Aug. 1988).

Searle, P. et al., "Absolute Configuration of Phorboxazoles A and B from the Marine Sponge *Phorbas* sp. 1. Macrolide and Hemiketal Rings," *J. Am. Chem. Soc.*, Vol. 118, No. 39, pp. 9422–9423 (Oct. 2, 1996).

Searle, P. et al., "Phorboxazoles A and B: Potent Cytostatic Macrolides from Marine Sponge *Phorbas* Sp.," *J. Am. Chem. Soc.*, vol. 117, No. 31, pp. 8126–8131, (Aug. 9, 1995).

Uckun, F. et al., "Anticancer Activity of Synthetic Analogues of the Phorboxazoles," *Bioorganic & Medicinal Chemistry Letters*, vol. 11, No. 9, pp. 1181–1183 (May 7, 2000).

Venstrom, K. et al., "Extracellular Matrix 2: Role of extracellular matrix molecules and their receptors in the nervous system," *The FASEB Journal*, vol. 7, No. 11, pp. 996–1003 (Aug. 1993).

Williams, D. et al., "Asymmetric Allylation. An Effective Strategy for the Convergent Synthesis of Highly Functionalized Homoallylic Alcohols," *Tetrahedron Letters*, vol. 39, pp. 7251–7254 (1998).

Wolbers, P. et al., "Structure–Activity Investigations of Analogues of the C15–C26 Phorboxazoles Segment," *Synlett*, No. 11, pp. 1808–1810 (Nov. 1999).

Ye, T. et al., "Synthetic Studies towards Phorboxazole A. A Concise Stereoselective Synthesis of the C20–C26 Pentasubstituted Oxane Ring Unit," *Tetrahedon Letters*, vol. 39, pp. 319–322 (1998).

* cited by examiner

Effect of phorboxazole A, 33-O-methyl-phorboxazole A and 45,46-dehydrombromo-phorboxazole A on mitochondrial transmembrane potential in acute lymphoblastic leukemia NALM-6 cells.

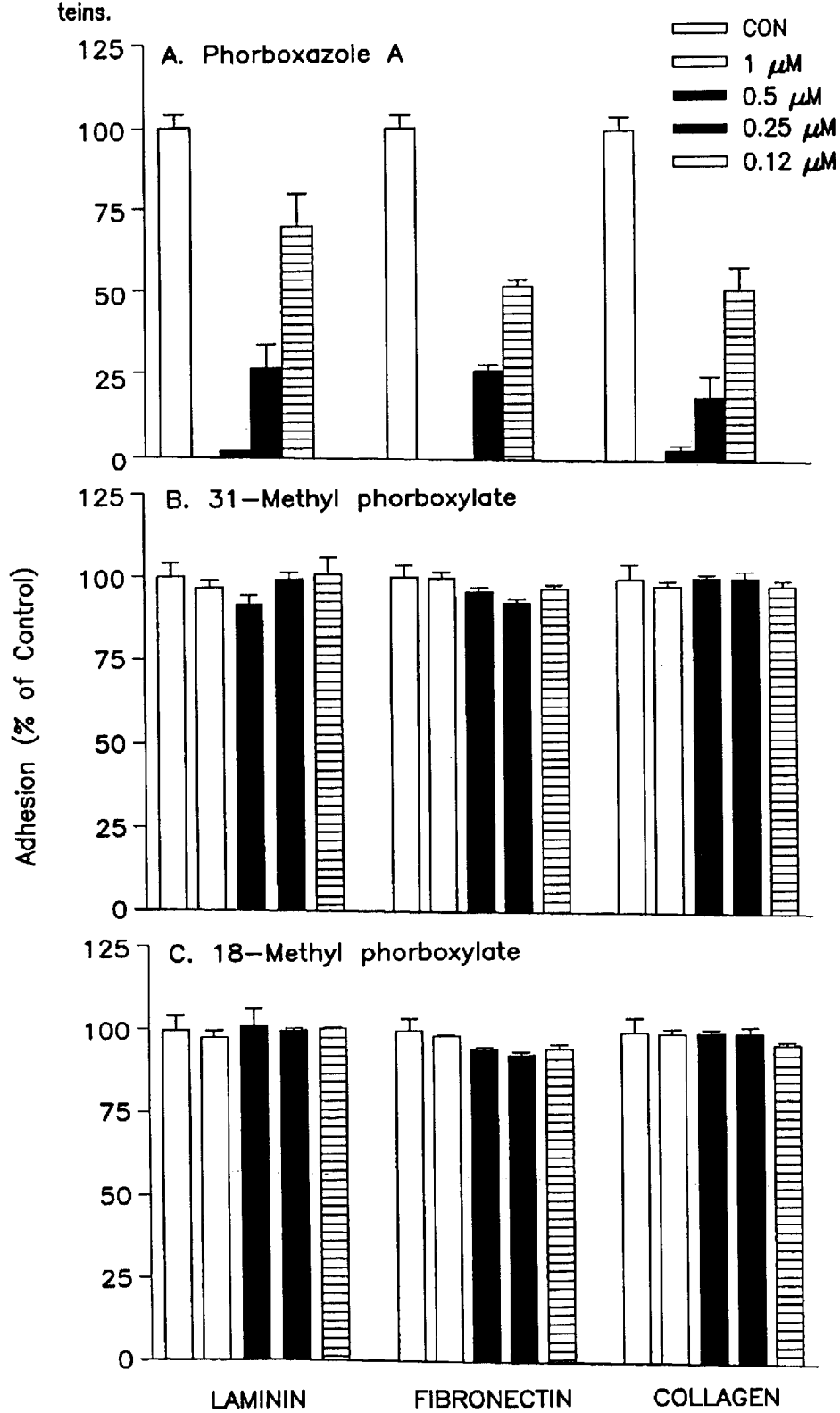
FIG. 3  Effect of phorboxazole A, 31-methyl phorboxylate and 18-methyl phorboxylate breast cancer BT-20 Cell-adhesion to extracellular matrix proteins.

PHORBOXAZOLE DERIVATIVES FOR TREATING CANCER

This application is a continuation of PCT/US00/31388, filed on Nov. 15, 2000, published in English on May 25, 2001 as WO 01/36048, and designating the United States, which claims benefit of U.S. Provisional Application No. 60/165,452, filed on Nov. 15, 1999.

FIELD OF THE INVENTION

This invention relates to the use of synthetic phorboxaxole A in the treatment of cancer and to novel phorboxazole A derivatives that are useful as anti-cancer agents. In particular, the invention includes novel dehydrobromo and mixed methyl ketal derivatives having potent cytostatic and apoptotic effects against cancer cells, including human leukemia, breast cancer, prostate cancer and brain cancer cells. Novel phorboxazole derivative compounds of the invention inhibit migration of cancer cells through extracellular matrix, an activity required for tumor metastisis. In addition, the invention relates to methods of using synthetic phorboxaxole A and novel phorboxazole A derivatives of the present invention as therapeutic agents.

BACKGROUND OF THE INVENTION

Phorboxazoles are natural products isolated from the Indian Ocean sponge Phorbas sp (Searle, et al., 1995, *J. Am. Chem. Soc.*, 117, 8126–8131). They have exhibited potent cytostatic activity against a variety of human solid tumor cell lines (Searle, et al., 1996, *J. Am. Chem. Soc.*, 118, 9422–9423). The precise phorboxazole mechanism of action is unknown, however, they do not act as microtubule-targeted antimitotics and appear to arrest cell cycle at S phase (Molinski, T. F., 1996, *Tetrahedron Letters*, 37, 7879–7880).

The use of phorboxazoles as anti-cancer agents is limited due to problems associated with isolating the compounds from their natural source. Many marine sponge-derived natural products are the result of biosynthesis by symbiotic microorganisms that may only be temporarily associated with the sponge and not amenable to laboratory culture. Furthermore, the supply of marine sponges, the natural source of phorboxazoles, is limited and subject to harvesting restrictions. Hence, a synthetic route to provide phorboxazoles and active anti-cancer phorboxazole derivatives is needed to exploit the potential of these therapeutic agents.

Synthetic routes to phorboxazole and phorboxazole derivatives are needed to allow investigation of structure-activity relationships and the scope of cellular responses with respect to these compounds. In particular, synthetic phorboxazole compounds are needed to elucidate and confirm the structure of phorboxazole compounds associated with therapeutic activities. Because phorboxazoles have not been fully characterized, confirmation of the proposed chemical structures is needed to usefully apply this technology. Useful structures for phorboxazole compounds can be confirmed by their synthetic production and analysis of the activities of the synthesized compounds.

Phorboxazole compounds are complex and difficult to synthesize. The first synthetic phorboxazole compound was produced as described in Forsyth et.al., 1988, J.Am. Chem. Soc. 120:5597. It has now been determined, as described in the Examples below, that a synthetic phorboxazole A, having the structure (I) shown below, is active as a cytotoxic agent. In addition, specific derivatives of the synthetic phorboxazole A also have demonstrated cytoxic activity. Specific derivatives of the synthetic phorboxazole A that may not be cytotoxic, are demonstrated in the Examples below to inhibit cell migration and invasion, and thus provide useful agents to prevent cancer cell metastases.

SUMMARY OF THE INVENTION

Synthetic phorboxazole A having the chemical structure (I) shown below and specific phorboxazole A derivatives were synthesized and examined for their cytotoxic effects on cancer cells, including human leukemia, breast cancer, prostate cancer and brain cancer cells. Synthetic phorboxazole A and novel dehydrobromo and mixed methyl ketal derivatives of phorboxazole A were found to exhibit potent cytotoxic activity against cancer cells at nanomolar concentrations.

Generally, the present invention relates to novel compounds and compositions having potent cytotoxic activity against cancer cells. One embodiment relates to compositions containing an effective cytotoxic or inhibitory amount of a synthetic phorboxazole A and of a novel dehydrobromo or mixed methyl ketal derivative of phorboxazole A. The cytotoxic compounds of the invention include those having the following formulae:

I. Phorboxazole A

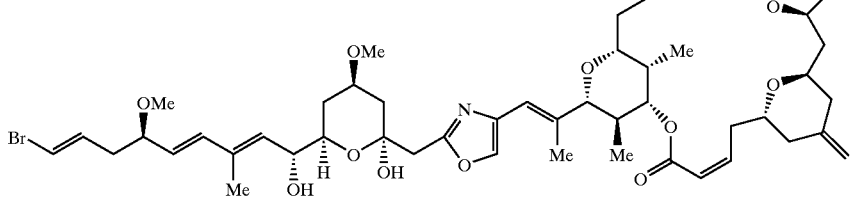

II. 45,46-dehydrobromo-Phorboxazole A

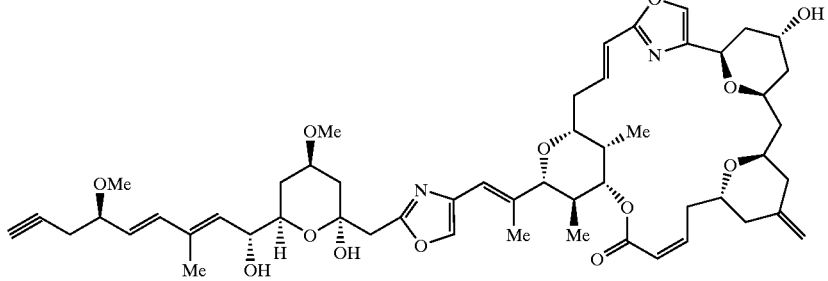

and

-continued

III. 33-O-methyl-Phorboxazole A

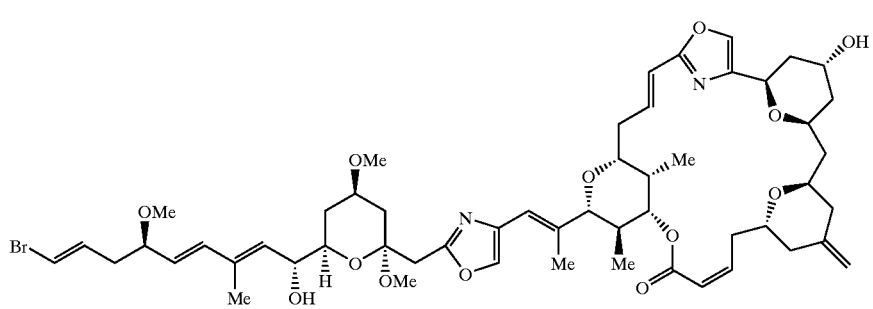

Another embodiment of the present invention provides compositions formulated for delivery of the cytotoxic phorboxazole compounds to a subject as a pharmaceutical composition.

A further embodiment of the present invention provides methods to inhibit the growth or induce apoptosis of cancer cells, by administering to a subject or contacting cancer cells with an effective amount of a compound or composition of the present invention.

Yet another embodiment of the present invention provides specific derivatives of Phorboxazole A and methods to inhibit adhesion and migration of cancer cells through extracellular matrix, an activity required for tumor metastisis. The structures and activities of these compounds are described in the Examples below.

A further embodiment of the present invention provides a method for the synthesis of Phorboxazole A derivatives as described in the Examples below.

The above summary of the present invention is not intended to describe each disclosed embodiment or every implementation of the present invention. The Figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying Figures, in which:

FIG. 3 are bar graphs showing the effect of synthetic phorboxazole A and phorboxazole A derivatives on cell adhesion to extracellular matrix proteins.

DETAILED DESCRIPTION OF THE INVENTION

Figure 1A:
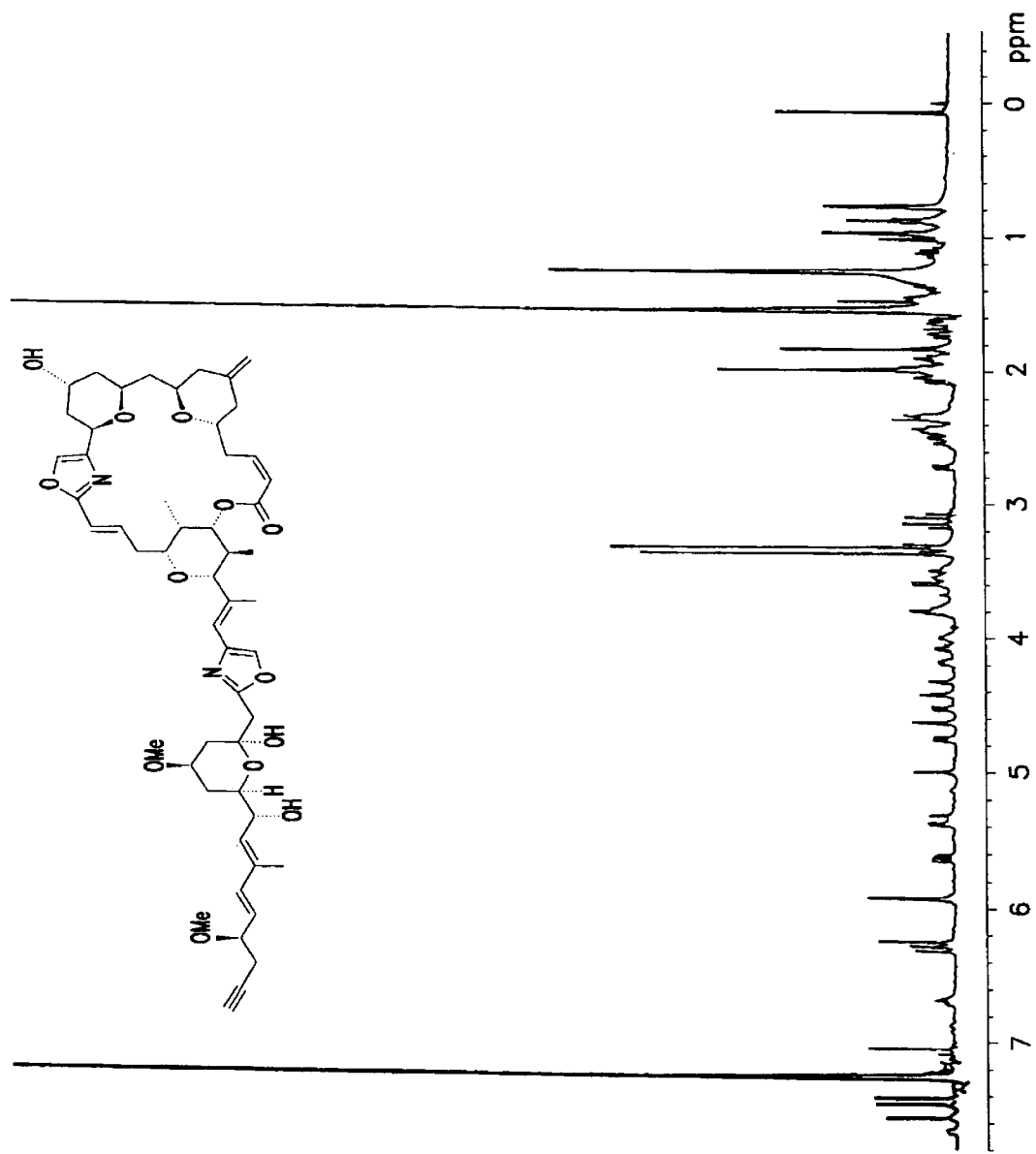
FIG. 1A is the $^1$H NMR spectra of 45,46-dehydrobromo-phorboxazole A.

The present invention includes synthetic phorboxazole A having the structure (I) shown above, as a cytotoxic compound, useful in pharmaceutical compositions to arrest cell growth and induce apoptosis in cells. The examples below establish synthetic phorboxazole A as a useful therapeutic agent.

The invention also provides novel phorboxazole A derivatives having potent activity as cytotoxic agents against cancer cells, including leukemia, prostate cancer, breast cancer and brain cancer cells, and particularly against multi-drug resistant cancer cells, for example, human B-lineage acute lymphoblastic leukemia cells, glioblastoma cells, and BT-20 human breast cancer cells. In addition, specific novel phorboxazole A derivatives of the invention are potent inhibitors of tumor cell adhesion and migration, activities required for tumor cell metastases. While the present invention is not so limited, an appreciation of various aspects of the invention will be gained through the description and the Examples provided below.

Definitions

All scientific and technical terms used in this application have meanings commonly used in the art unless otherwise specified. As used in this application, the following words or phrases have the meanings:

As used herein, "pharmaceutically acceptable carrier" includes any material which, when combined with a compound of the invention, allows the compound to retain biological activity, such as the ability to induce apoptosis of cancer cells, and is non-reactive with the subject's immune system. Examples include, but are not limited to, any of the standard pharmaceutical carriers such as a phosphate buffered saline solution, water, emulsions such as oil/water emulsions, and various types of wetting agents. Also included are pegalation and liposome systems as useful carriers of the compositions of the invention. In addition, carrier molecules such as specific anti-cancer antigen antibodies and ligands such as EGF can be used to carry the compound to the target cells. Compositions comprising such carriers, including composite molecules, are formulated by well known conventional methods (see, for example, Remington's Pharmaceutical Sciences, Chapter 43, 14th Ed., Mack Publishing Co., Easton, Pa.).

"Treating", "Treatment", or "to treat" in the context of this invention means to inhibit or block at least one symptom that characterizes a pathologic condition, in a mammal threatened by, or afflicted with, the condition. In the context of cancer therapy, treatment includes prevention of tumor growth, reduction of tumor size, enhanced tumor cell death, and increased apoptosis. Treatment also includes the prevention of cancer cell adhesion and migration into tissues.

"Inhibit" means to reduce by a measurable amount, or to prevent entirely.

"Multi-Drug Resistant Cancer Cells" means one or more type of cancer cell which is resistant to treatment with one or more chemotherapeutic agent.

"Therapeutically effective amount" is a dose which provides some therapeutic benefit on administration, including, in the context of the invention, inhibition of cancer cell growth and/or proliferation; prevention or inhibition of apoptosis; reduction in tumor mass; prevention of cancer cell adhesion and/or migration; and increase in patient longevity.

"Prodrug" is a substitution group which facilitates use of a compound of the invention, for example by facilitating entry of the drug into cells or administration of the compound to a patient. The prodrug moiety may be cleaved from the compound, for example by enzyme cleavage in vivo. Examples of prodrug moieties include phosphate groups, peptide linkers, and sugars, which moieties can be hydrolyzed in vivo to release the compound of the invention.

Compounds of the Invention

Synthetic Phorboxazole A, prepared according to the method described in Forsyth et.al. 1998, *J. Am. Chem. Soc.* 120: 5597, has the chemical structure shown below in formula I. Novel cytotoxic phorboxazole A derivatives of the invention have the structures represented by the following formulae II and III:

values. In contrast, none of the other six synthetic analogs showed cytotoxic activity. The three active cytotoxic compounds also inhibited clonic growth and induced apoptosis in the cancer cells.

The data suggests the macrolide, central oxazole, polyene side chain, and acrylate moieties of Phorboxazole A are necessary for potent activity. Modification in these areas essentially eliminates any cytotoxic activity. Molecular modeling indicates that the conformation of the 2,3-dihydro-Phorboxazole A is similar to that of the parent compound.

The high activities of the 45,46-dehydrobromo-Phorboxazole and 33-O-methyl-Phorboxazole A allows for simplification of the preparative chemistry required to access novel cytotoxic agents. A The high yield of C29–C31 oxazole formation and opportunities for terminal carbon—

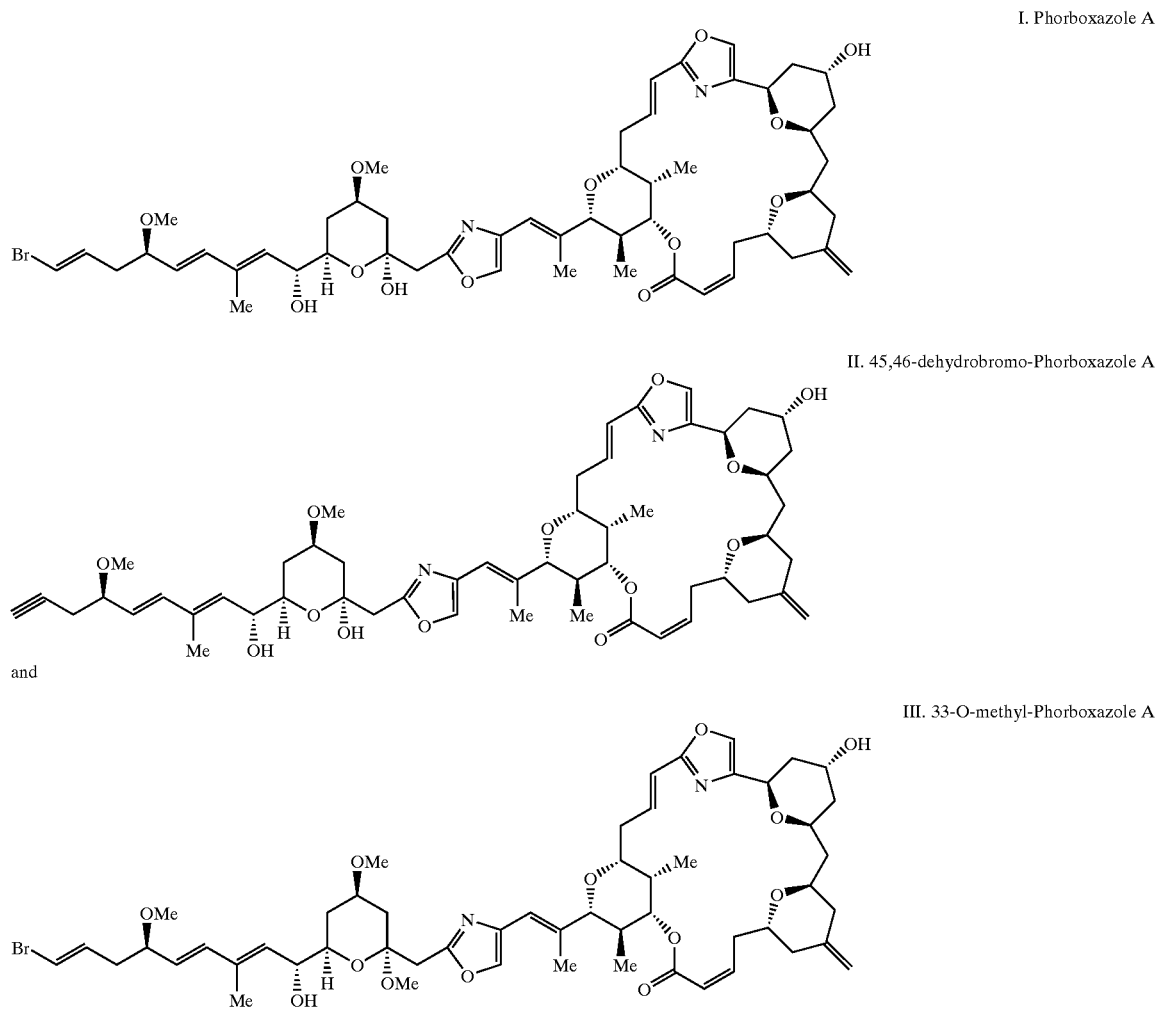

I. Phorboxazole A

II. 45,46-dehydrobromo-Phorboxazole A and

III. 33-O-methyl-Phorboxazole A

Cytotoxic Compounds

As shown in the Examples below, synthetic Phorboxazole A and several distinct synthetic analogs were tested for cytotoxic activity. Synthetic Phorboxazole A inhibited growth of leukemia, breast, and brain tumor cells, for example as demonstrated in MTT assays. Analogs 45,46-dehydrobromo-Phorboxazole A, which bears an alkyne in place of the C45–C46 terminal bromide, and 33-O-methyl-Phorboxazole A, which has a mixed methyl ketal instead of the C33 hemiketal also inhibited cancer cell growth in a concentration-dependent fashion with low, nanomolar $IC_{50}$ carbon bond formation via Sonogishira type-couplings make the dehydrobromo-analog particularly attractive for the production of an anti-cancer drug.

Useful compounds of the invention are tested for cytotoxicity as described in the Examples below. Such tests include inhibition of cologenic growth of human cancer cell lines and MTT assays to determine inhibition of cancer cell proliferation and induction of apoptosis. These assays are well known in the field of cancer therapeutics, and have been well established as effective assays for predicting useful pharmaceutical agents for the treatment of cancer.

Compounds for Inhibiting Adhesion/Migration

The Examples below demonstrate the effectiveness of synthetic Phorboxazole A and specific derivatives of Phorboxazole A, which derivatives may or may not be cytotoxic, as inhibitors of cancer cell adhesion to extracellular matrix and of tumor cell migration. Particularly potent and useful inhibitory compounds are synthetic Phorboxazole A, and the following non-cytotoxic derivatives: 29-Phorboxamide A, C-31-methyl-Phorboxylate; and 18-methyl-Phorboxylate.

include inhibition of cell binding to extracellular matrix proteins in the presence of the inhibitory compound as compared with a non-inhibitory control, and inhibition of cancer cell invasion into Matrigel™ Matrix according to the method published by Albini et.al., 1987, *Cancer Res.* 47:3239. These assays are well known in the field of cancer therapeutics, and have been well established as effective assays for predicting useful pharmaceutical agents for inhibition of cancer cell metastasis.

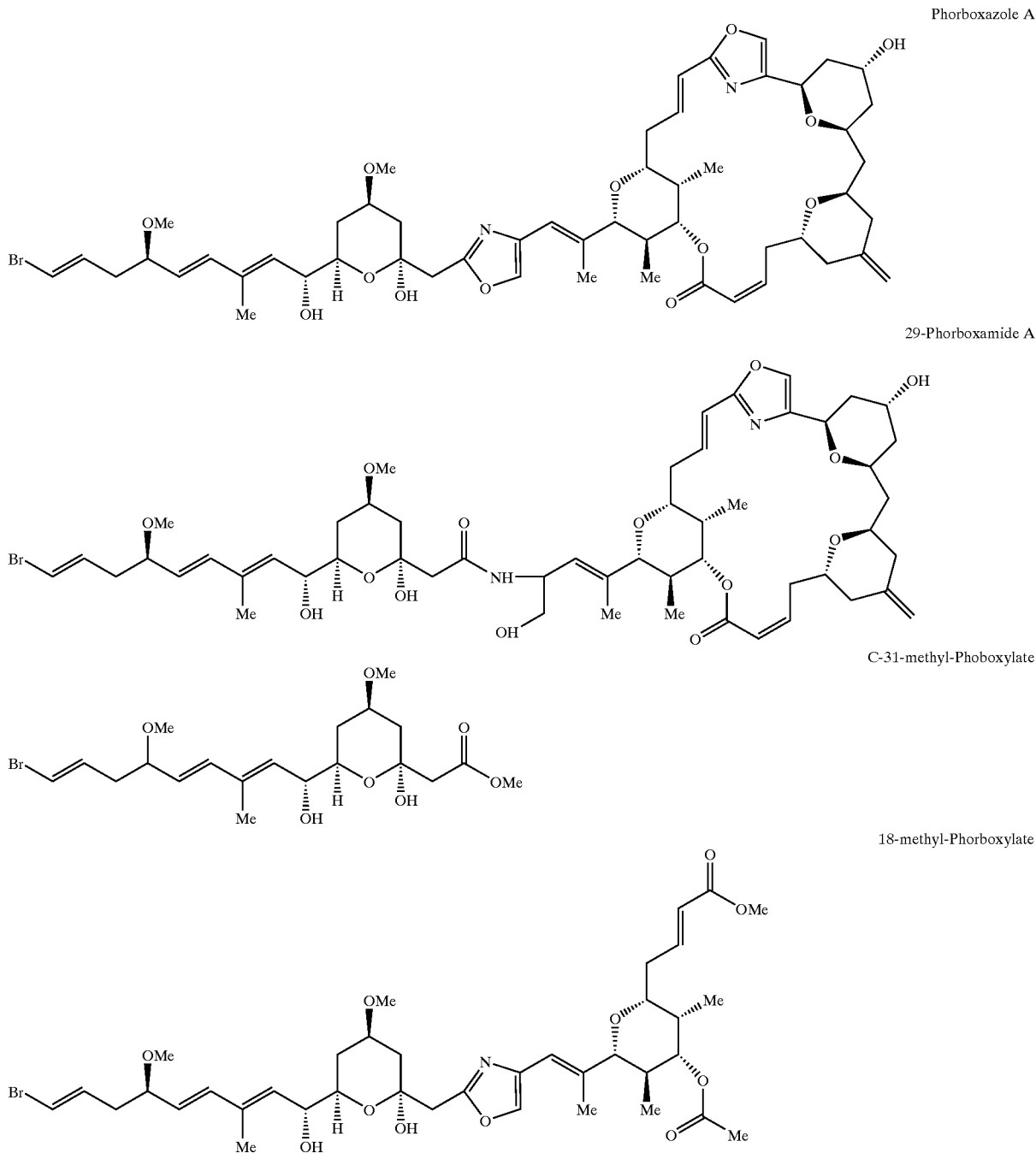

Useful inhibitory compounds of the invention are tested for the ability to prevent adhesion/migration of cancer cells by assays described in the Examples below. Such assays In the method of the invention, cancer cells are contacted with approximately nanomolar concentrations of the inhibitory compounds to inhibit cancer cell adhesion and invasion/ migration into non-diseased tissue. This is important, for example, during ablation surgery when cells may be dispersed. Adhesion of cells to extracellular matrix (ECM) proteins coupled with the aggressive malignant nature of some cancer cells can result in new tumor growth at the adhesion site. Inhibition of adhesion and migration by administering the compounds of the invention can thereby inhibit new tumor growth.

Synthesis of Novel Phorboxazole A Derivatives

Synthetic Phorboxazole A and derivatives can be synthesized as described below. Synthesis of phorboxazole A having the structural formula I shown above, is described in Forsyth, et al., 1998, *J. Am. Chem. Soc.*, 120, 5597–5598. The specific syntheses of 45,46-dehydrobromo-phorboxazole A and of 33-O-methyl-phorboxazole A is described below (see Synthetic Schemes I and II respectively).

45,46-Dehydrobromo-phorboxazole A was prepared as described in the Ph.D. thesis of Dr. Chi Song Lee (University of Minnesota, May 21, 1999 "Synthesis of the C18–C30 fragment of Phorboxazole A and optimization of the Total Synthesis") in a manner similar to that used for the total syntheses of phorboxazole A. This involved coupling of the C1–C30 intermediate, as described in Dr. Lee's thesis, with the corresponding C31 –C46 dehydrobromo-intermediate that was prepared as described in the Ph.D. thesis of Dr. Feryan Ahmed (University of Minnesota _____, 1999, "Synthesis of the C31 –C46 Fragment of Phorboxazole A"). Attachment of the C31–C46 fragment to the C1–C30 domain was preceded by selective removal of the t-Boc group from the C1–C30 domain by treatment with TFA in $CH_2CH_2$ at 0° C. The vicinal amino alcohol was then coupled to the C31–C46 carboxylic acid. The resulting hydroxy amide was then subjected to a step-wise oxidation-cyclodehydration process (as described in Wipf, P.; Miller, C. P.; 1993, *J. Org. Chem.*, 58:3604 and Wipf, P.; Lim, S.; *J. Am. Chem. Soc.*, 1995,117:558) that proceeded through a sensitive amide-aldehyde en route to the desired oxazole. The silyl ethers at C13 and C38 were cleaved with TBAF/ ethyl acetate and the C33-O-methyl acetal was hydrolyzed using 6% aqueous HCL to afford the desired 45,46-Dehydrobromo-phorboxazole A product.

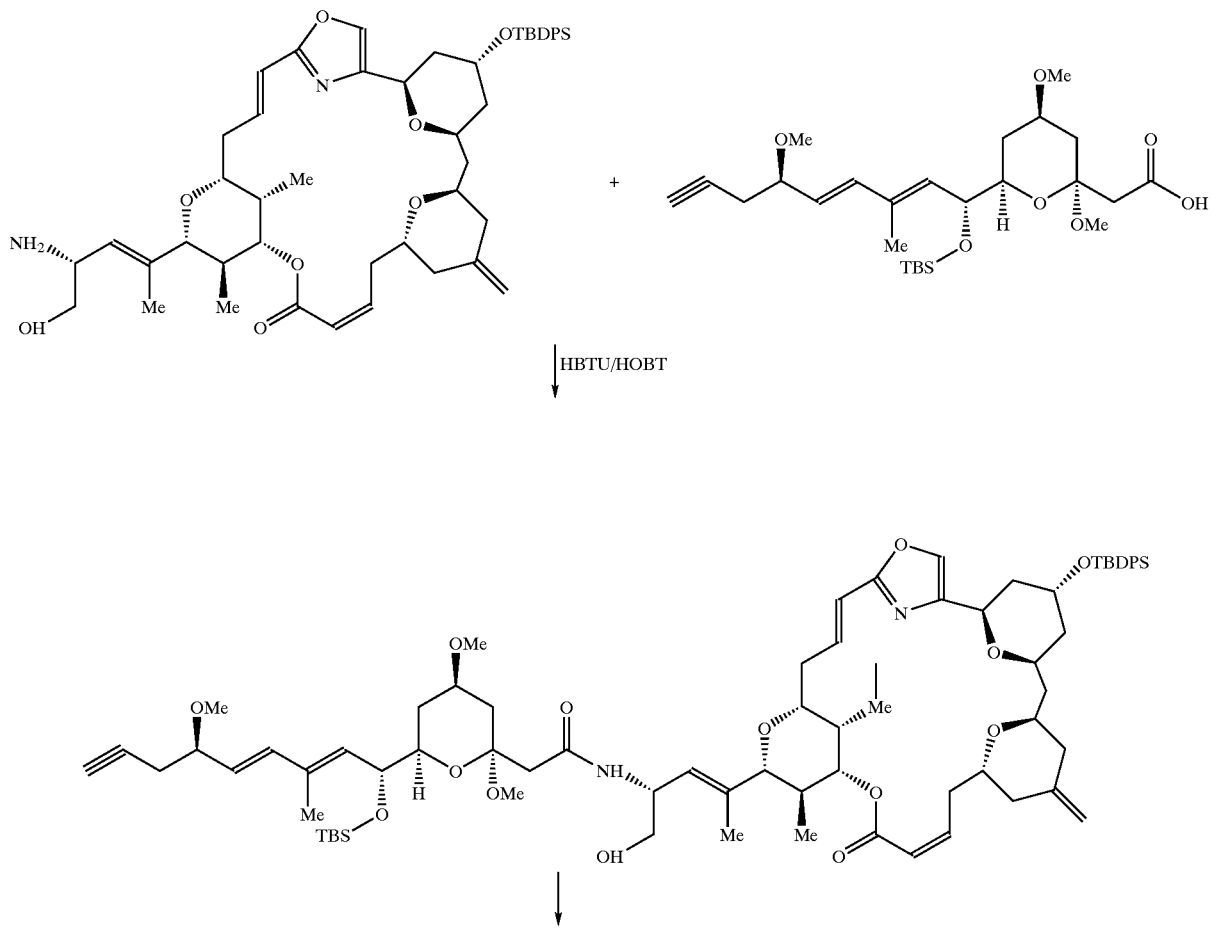

Synthetic Scheme I: 45, 46-dehydrobromo-phorboxazole A

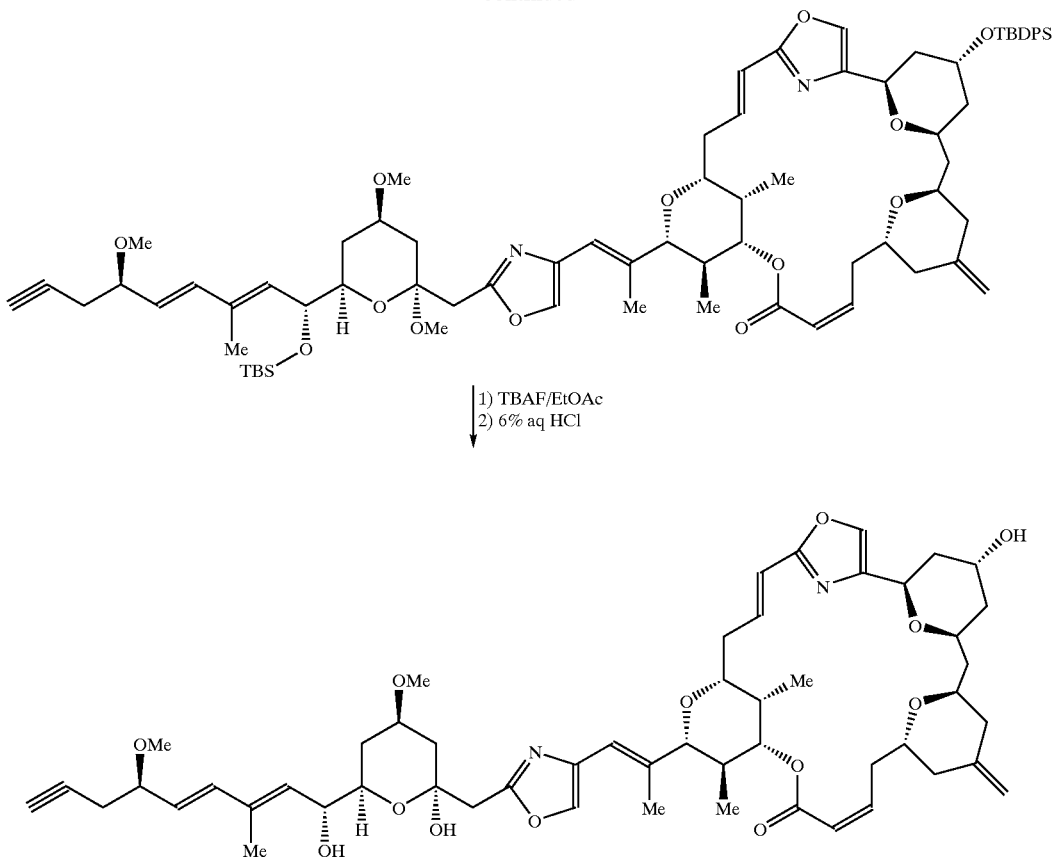

33-O-methyl-phorboxazole A was prepared generally following the procedure in Forsyth, et al., 1998, *J. Am. Chem. Soc.*, 120:5597. To obtain this compound, the final deprotection step (33-O-methyl-phorboxazole A with 6% aqueous HCl) was omitted from the synthesis route to phorboxazole A. The C31–C46 synthetic intermediate (described in Ahmed and Forsyth, 1998, *Tetrahedron Lett.*, 39:183) containing the vinyl bromide terminus was coupled with the C1–C30 amino alcohol intermediate and the product advanced to the desired 33-O-methyl-phorboxazole A product as described in the Forsyth, et al. paper. Specifically, after coupling of the C1–C30 domain containing the vinyl bromide terminus and C31–C46 domain, the resulting hydroxy amide was then subjected to a step-wise oxidation-cyclodehydration process (as described in Wipf, P.; Miller, C. P.; 1993, *J. Org. Chem.*, 58:3604 and Wipf, P.; Lim, S.; *J. Am. Chem. Soc.*, 1995, 117:558) that resulted in the desired oxazole. The silyl ethers at C13 and C38 were then cleaved with TBAF/ethyl acetate to afford 33-O-methyl-phorboxazole.

Synthetic Scheme II: 33-O-methyl-phorboxazole A

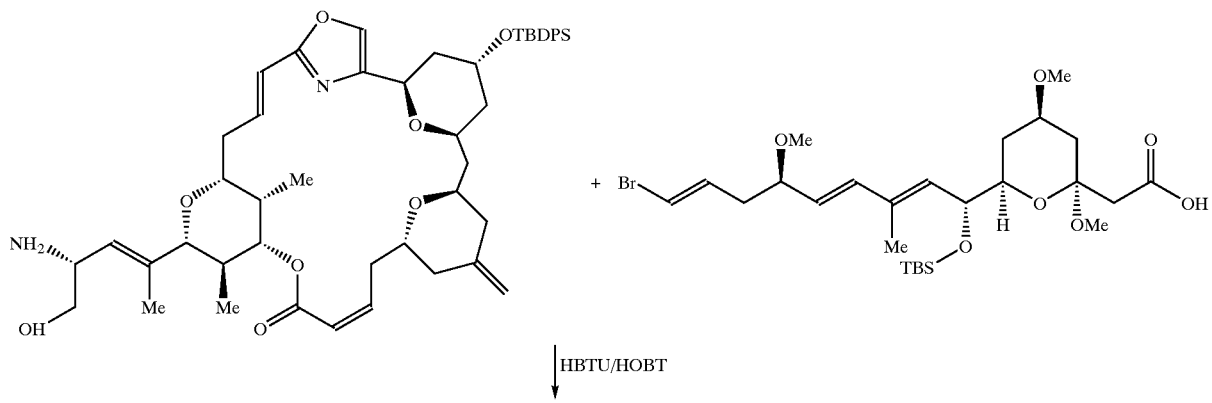

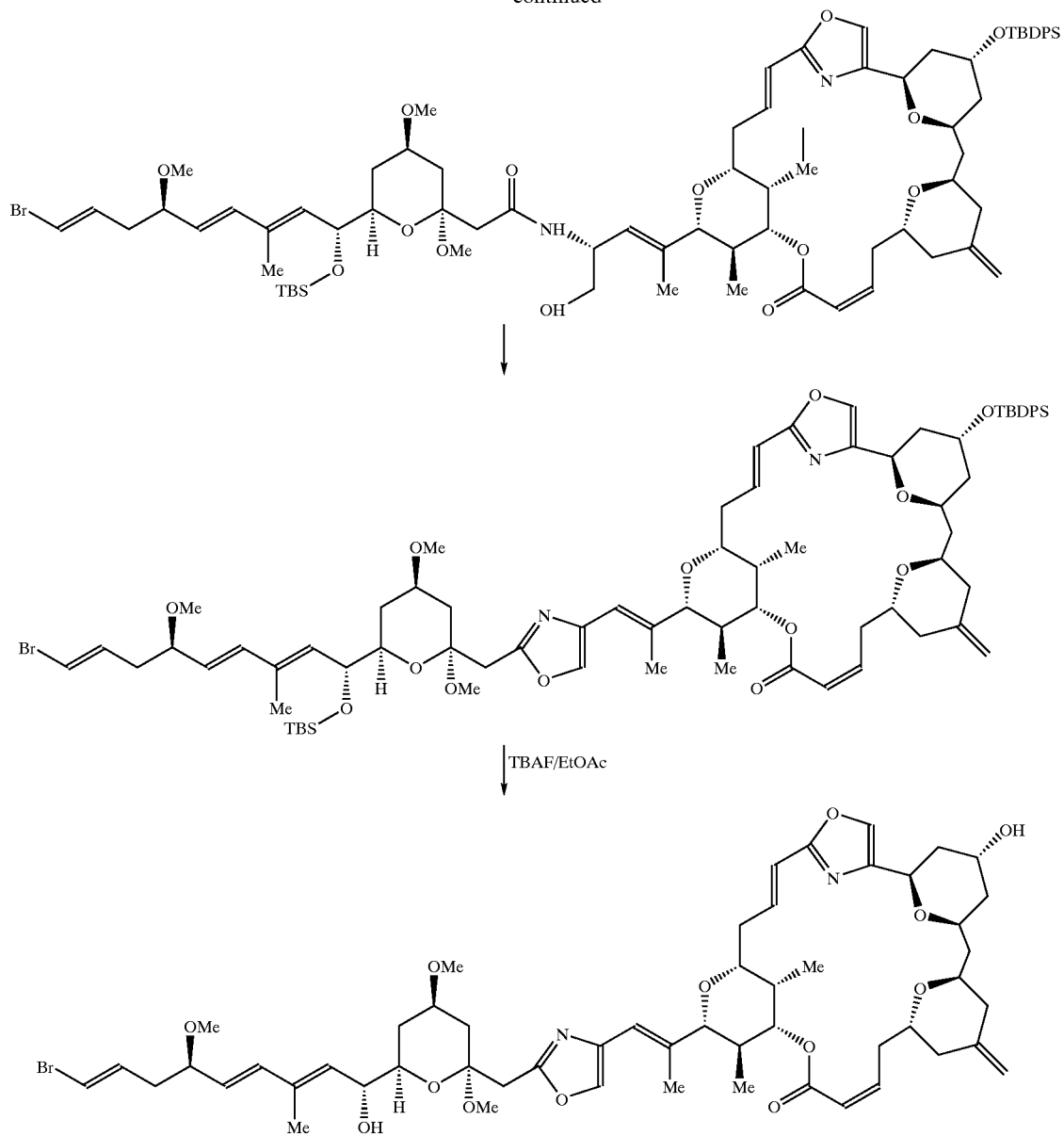

Adhesion and migration-inhibiting derivatives, 29-Phorboxamide A, C-31-methyl-Phorboxylate; and 18-methyl-Phorboxylate, are synthesized as described in Forsyth, et al., 1998, *J. Am. Chem. Soc.*, 120, 5597–5598.

Prodrug

The term "prodrug" is meant to define a conjugate molecule, where the two molecular species are a phorboxazole A derivative and a moiety which renders the conjugate biologically inert yet which has pharmacological activity upon bioactivation. Prodrugs include, for example, phorboxazole A derivatives covalently attached to molecular species which can be cleaved, for example, enzymatically (i.e the cleavage of ester linkages by esterases) or through acid catalyzed hydrolysis. Prodrugs useful in the invention include those that contain, for example, an ester or amide, N-mannich base, N-hydroxymethyl derivative, N-acyl derivative, or oxazolidine linkage between the phorboxazole A derivative and the other moiety.

Administration Methods

The conjugates of the present invention can be formulated as pharmaceutical compositions and administered to a mammalian host, including a human patient in a variety of forms adapted to the chosen route of administration and suitable for administration of the small molecule or its conjugate.

It is preferred that the compositions of the present invention be administered parenterally, i.e., intravenously or intraperitoneally, by infusion or injection. In one embodiment of the invention, the compounds may be administered directly to a tumor by tumor injection; by injecting the compound into the brain, e.g., into the ventricular fluid; or by systemic delivery by intravenous injection. The compounds of the invention, including the conjugates, are of a size and composition expected to have ready access to the brain across the blood-brain barrier.

Solutions or suspensions of the conjugates can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin.

Sterile injectable solutions are prepared by incorporating the conjugates in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Cancer Treatment

For purposes of this invention, a method of treating cancer includes contacting cancer cells with a compound of the invention in order to achieve an inhibition of cancer cell growth, a killing of cancer cells, and/or increased patient survival time. Treatment of cancer, by the method of the invention, also includes the prevention of the adhesion and migration of cancer cells, thereby inhibiting metastases.

The cytotoxic and adhesion/migration-inhibiting compounds of the invention are suitable for use in mammals. As used herein, "mammals" means any class of higher vertebrates that nourish their young with milk secreted by mammary glands, including, for example, humans, rabbits, and monkeys.

Apoptosis

Apoptosis, or programmed cellular death, is an active process requiring new protein synthesis. Typically, the process requires ATP, involves new RNA and protein synthesis, and culminates in the activation of endogenous endonucleases that degrade the DNA of the cell, thereby destroying the genetic template required for cellular homostasis. Apoptosis is observed in controlled deletion of cells during metamorphosis, differentiation, and general cell turnover and appears normally to be regulated by receptor-coupled events. For these reasons, apoptosis has been called "programmed cell death" or "cell suicide." While every cell likely has the genetic program to commit suicide, it is usually suppressed. Under normal circumstances, only those cells no longer required by the organism activate this self-destruction program.

Apoptotic cell death is characterized by plasma membrane bleeding, cell volume loss, nuclear condensation, and endonucleolytic degradation of DNA at nucleosome intervals. Loss of plasma membrane integrity is a relatively late event in apoptosis, unlike the form of cell death termed necrosis, which can be caused by hypoxia and exposure to certain toxins and which is typically characterized early-on by increased membrane permeability and cell rupture.

Adhesion/Migration

Adhesion is meant to include that activity of a cell, such as a cancer cell, by which it adheres to extracellular matrix proteins, including laminin, fibronectin, and collagen. Adhesion assays are known, and include, for purposes of this invention, the adherence of tumor cells to plates coated with extracellular matrix proteins.

Migration is meant to include that activity of tumor cells by which they migrate through extracellular matrix and invade tissues. Assays for migration include the ability of cells to migrate through a matrix formed of extracellular matrix, such as MATRIGEL™ matrix.

Useful Dose

When used in vivo to selectively kill cancer cells or to inhibit cancer cell adhesion/migration, the administered dose is that effective to have the desired effect, e.g., sufficient to reduce or eliminate cancer cells, or sufficient to inhibit adherence/migration of tumor cells. Appropriate amounts can be determined by those skilled in the art, extrapolating using known methods and relationships, from the in vitro data provided in the Examples.

In general, the dose of the novel phorboxazole A derivatives effective to achieve cancer cell apoptosis, inhibition of cancer cell growth, and increased subject survival time, is that which administers nanomolar amounts of the compound to the cells, preferably 100 nanomolar or greater. The required dose can be lessened by conjugation of the compound to a targeting moiety, for example, to preferably 50 nanomolar or greater concentrations.

For cell adhesion and migration inhibitory activities, the compound is administered generally at higher dosages, in the range of 200 nanomolar or less.

The effective dose to be administered will vary with conditions specific to each patient. In general, factors such as the disease burden, tumor location (exposed or remote), host age, metabolism, sickness, prior exposure to drugs, and the like contribute to the expected effectiveness of a drug. One skilled in the art will use standard procedures and patient analysis to calculate the appropriate dose, extrapolating from the data provided in the Examples.

In general, a dose which delivers about 1–100 mg/kg body weight is expected to be effective, although more or less may be useful.

In addition, the compositions of the invention may be administered in combination with other anti-cancer therapies. In such combination therapy, the administered dose of the phorboxazole derivatives would be less than for single drug therapy.

EXAMPLES

The invention may be further clarified by reference to the following Examples, which serve to exemplify some of the preferred embodiments, and not to limit the invention in any way.

Example 1

Synthesis of Phorboxazole Derivatives

All chemicals were purchased from the Aldrich Chemical Company, Milwaukee, Wis., and were used directly for synthesis. Anhydrous solvents such as acetonitrile, methanol, ethanol, ethyl acetate, tetrahydrofaran, chloroform, and methylene chloride were obtained from Aldrich as sure seal bottles under nitrogen and were transferred to reaction vessels by cannulation. All reactions were carried out under a nitrogen atmosphere.

45,46-dehydrobromo-phorboxazole A

The 45,46-dehydrobromo-phorboxazole A derivative was prepared as described above in Synthetic Scheme I. Specifically, attachment of the C31–C46 fragment, prepared as described in the Ph.D. thesis of Dr. Feryan Ahmed (University of Minnesota _____, 1999, "Synthesis of the C31–C46 Fragment of Phorboxazole A"), to the C1–C30 domain, prepared as described in the Ph.D. thesis of Dr. Chi Song Lee (University of Minnesota, May 21, 1999 "Synthesis of the C18–C30 fragment of Phorboxazole A and optimization of the Total Synthesis, was preceded by selective removal of the t-Boc group from the C1–C30 domain by treatment with TFA in $CH_2Cl_2$ at 0° C. The resulting vicinal amino alcohol was then coupled to the C31–C46 carboxylic acid using HBTU/HOBT as described in Knorr, et al., 1989, *Tetrahedron Lett.*, 30:1927 and Konig, et al., 1970, *Ber. Dtsch. Chem. Ges.*, 103:2034. The resulting hydroxy amide was then subjected to a step-wise oxidation-cyclodehydration process (as described in Wipf, P.; Miller, C. P.; 1993, *J. Org. Chem.*, 58:3604 and Wipf, P.; Lim, S.; *J. Am. Chem. Soc.*, 1995, 117:558) that proceeds through an amide-aldehyde en route to the desired oxazole. The silyl ethers at C13 and C38 were then cleaved with TBAF/ethyl acetate.

To a stirred solution of the resultant diol (0.4 mg, 0.4 $\mu$mol) in THF (0.5 mL) was added 6% aqueous HCl (0.1 mL). The mixture was stirred for 30 hours and washed with saturated aqueous $NaHCO_3$ (0.5 mL). The aqueous phase was extracted with ethyl acetate (5×1 mL) and the combined extracts were dried over Na2SO$_4$, filtered and concentrated. Preparative thin-layer chromatography (ethyl acetate) of the residue gave the desired product (0.2 mg, 0.2 $\mu$mol, 51%) as a white film: R$_f$0.45 (ethyl acetate-methanol, 15:1 v/v). H NMP (CDCl$_3$, 500 MHz, partial interpretation) δ7.58 (s, 1H), 7.43 (s, 1H), 6.30 (d, J=18.5 Hz), 6.25 (s, 1H), 5.92 (m, 2H), 3.37 (s, 3H), 3.30 (s, 3H). By comparison with the characterization data of phorboxazole A, only two singlets appear between 3.40–3.30 ppm in the $^1$H NMR spectrum of the product which indicates hydrolysis of the mixed methyl acetal. FIG. 1A is the $^1$H NMR spectrum of the 45,46-dehydrobromo-phorboxazole A product.

33-O-methylphorboxazole A

The 33-O-methylphorboxazole A derivative was prepared as described above in Synthetic Scheme I. Specifically, the C31–C46 synthetic intermediate (described in Ahmed and Forsyth, 1998, *Tetrahedron Lett.*, 39:183) containing the vinyl bromide terminus was coupled with the C1–C30 amino alcohol intermediate and the product advanced to the desired 33-O-methyl-phorboxazole A product as described in the Forsyth, et al. paper. Specifically, after coupling of the C1–C30 domain containing the vinyl bromide terminus and C31–C46 domain, the resulting hydroxy amide was then subjected to a step-wise oxidation-cyclodehydration process (as described in Wipf, P.; Miller, C. P.; 1993, *J. Org. Chem.*, 58:3604 and Wipf, P.; Lim, S.; *J. Am. Chem. Soc.*, 1995, 117:558) that resulted in the desired oxazole.

Figure 1B:
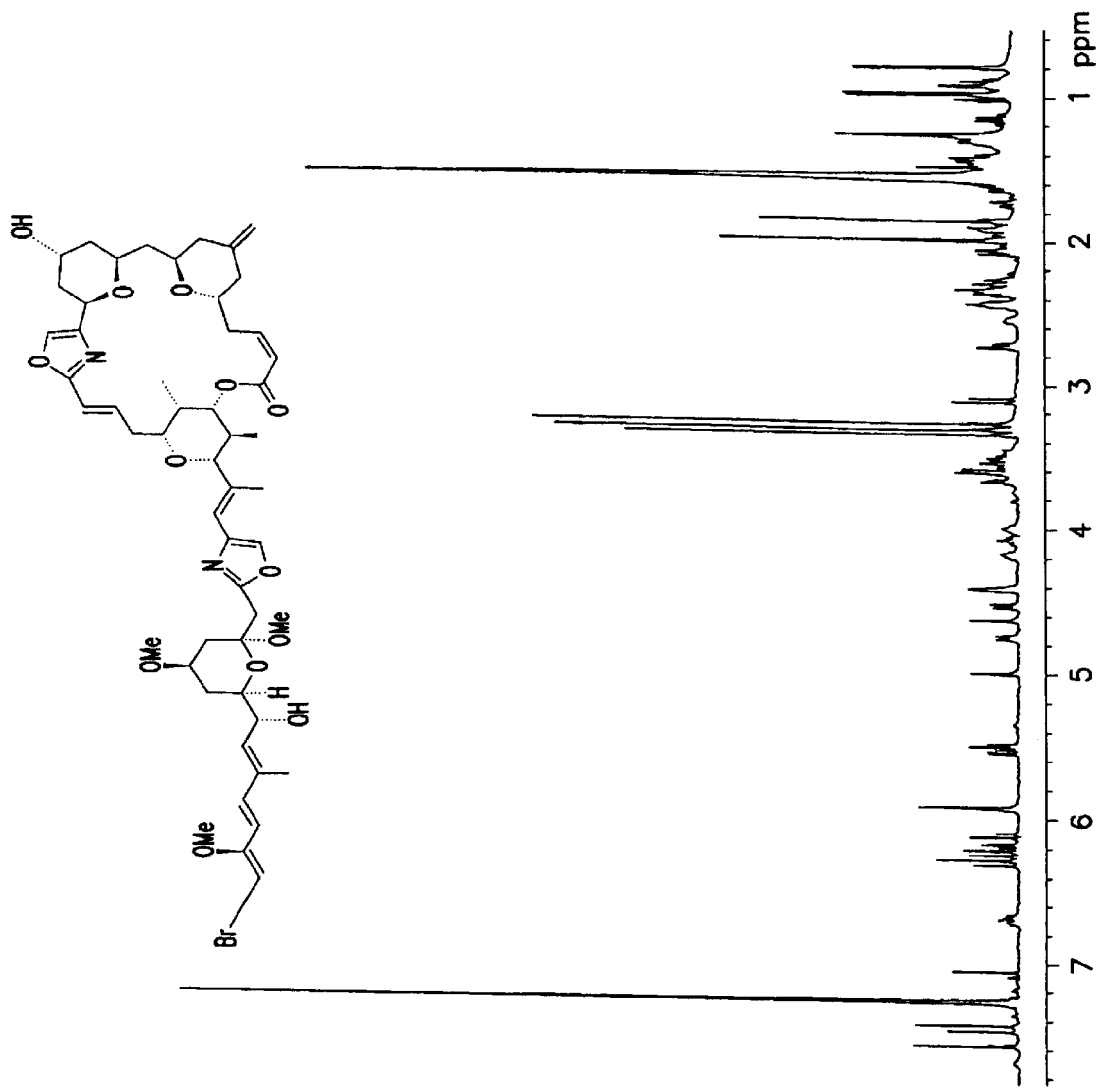
FIG. 1B is the $^1$H NMR spectra of 33-O-methyl-Phorboxazole A.

To a stirred solution of the desired oxazole intermediate (0.8 mg, 0.6 $\mu$mol) in ethyl acetate (1 mL) was added TBAF (0.2 mL of a 1.0 M solution in THE, 0.2 mmol). The mixture was stirred for 2 days, and washed with saturated aqueous NH$_4$Cl (0.5 mL). The aqueous phase was extracted with ethyl acetate (5×1 mL), and the combined extracts were dried over Na$_2$SO$_4$, filtered and concentrated. Silica gel column chromatography (ethyl acetate) of the residue afforded the desired product (0.5 mg, 0.4 $\mu$mol, 80%) as a white film: R$_f$ 0.46 (ethyl acetate-methanol, 15:1, v/v); $^1$H NMR (CDCl$_3$, 500 MHz, partial data) δ7.58 (s, 1H), 7.43 (s, 1H), 5.92 (m, 2H), 3.34 (s, 3H), 3.31 (s, 3H), 3.27 (s, 3H). By comparison with the characterization data of the oxazole intermediate, the signals at 7.65, 7.40, 1.09, 0.89, 0.07 and 0.03 were absent in H NMR spectrum of the product, which indicates the loss of TBDPS and TBS groups. FIG. 1B is the $^1$H NMR spectrum of the 33-O-methylphorboxazole A product.

Example 2

Cytotoxicity of Synthetic Phorboxazole A and Derivatives

The cytotoxicity of synthetic Phorboxazole A and several various phorboxazole A derivative compounds against human leukemia, breast cancer and brain cancer cells were evaluated. The relative importance of particular substituent group on the compounds was also studied. The phorboxazole A derivative compounds, prepared as described above for Example 1, were tested, along with genistein as controls.

Cytotoxicity Assay

The cytotoxicity assay of synthetic Phorboxazole A and various derivative compounds against human tumor cells was performed using the MTT (3-[4,5-dimethylthiazol-2-yl]-2,5-diphenyl tetrazolium bromide) assay (Boehringer Mannheim Corp., Indianapolis, Ind.). Briefly, exponentially growing brain tumor cells were seeded into a 96-well plate at a density of 2.5×10$^4$ cells/well and incubated for 36 hours at 37° C. prior to drug exposure. On the day of treatment, culture medium was carefully aspirated from the wells and replaced with fresh medium containing the various phorboxazole A derivative compounds as well as the tyrosine kinase inhibitory isoflavone genistein (GEN) at concentrations ranging from 0.1 to 250 $\mu$M. Triplicate wells were used for each treatment.

Human glioblastoma cells U373 (brain cancer), human B-lineage acute lymphoblastic leukemia cells NALM-6, and human breast cancer cells BT-20 were obtained from American Type Culture Collection (Rockville, Md.) and maintained as a continuous cell line in Dulbecco's modified Eagles's medium supplemented with 10% fetal bovine serum and antibiotics.

The cells were incubated with the various compounds for 24–36 hours at 37° C. in a humidified 5% CO$_2$ atmosphere. To each well, 10 $\mu$l of MTT (0.5 mg/ml final concentration) was added and the plates were incubated at 37° C. for 4 hours to allow MTT to form formazan crystals by reacting with metabolically active cells. The fonnazan crystals were solubilized overnight at 37° C. in a solution containing 10% SDS in 0.01 M HCl. The absorbance of each well was measured in a microplate reader (Labsystems) at 540 nm and a reference wavelength of 690 nm. To translate the OD$_{540}$ values into the number of live cells in each well, the OD$_{540}$ values were compared to those on standard OD$_{540}$-versus-cell number curves generated for each cell line. The percent survival was calculated using the formula:

$$\% \text{ Survival} = \frac{\text{live cell number [test]}}{\text{live cell number [control]}} 100$$

The $IC_{50}$ values were calculated by non-linear regression analysis.

Synthetic Phorboxazole A exhibited potent cytotoxicity against a panel of nine multi-drug resistant human cancer cell lines, as shown in Table 1, below. Anti-cancer activity of the synthetic Phorboxazole A was confirmed by confocal laser scanning microscopy. Apoptosis was confirmed by TUNEL assays.

TABLE 1

| CELLS | $IC_{50}$[MTT] (nM) |
| --- | --- |
| NALM-6 (ALL) | 1.7 |
| BT-20 (breast cancer) | 3.4 |
| PC3 (prostate cancer) | 14.2 |
| DU-145 (prostate cancer) | 15.0 |

TABLE 1-continued

| CELLS | $IC_{50}$[MTT] (nM) |
| --- | --- |
| U373 (glioblastoma) | 6.7 |
| ARH77 (multiple myeloma) | 7.5 |
| HS-SULTAN (multiple myleoma) | 29.8 |
| U266BL (multiple myleoma) | 14.9 |
| RPMI-18226 (multiple myeloma) | 55.9 |

Table 2, below, shows the number and structure of 10 synthetic Phorboxazole A compounds synthesized and tested for anti-cancer activity. Cytoxicity is shown in Table 3, where the data is expressed as $IC_{50}$[MTT] for the 10 synthetic Phorboxazole A compounds tested. As shown in Table 3, the phorboxazole A derivatives, 45,46-dehydrobromo-phorboxazole A and 33-O-methyl-phorboxazole A were potent cytotoxic agents, whereas the remaining derivatives lacked cytotoxic activity. The rank order of sensitivity was Nalm-6>BT-20>U373. As shown below, the three active compounds also prohibited clonogenic growth of all three cancer cell lines.

TABLE 2

| Compound Number | Compound Name | Compound Structure |
| --- | --- | --- |
| 1 | Phorboxazole A | 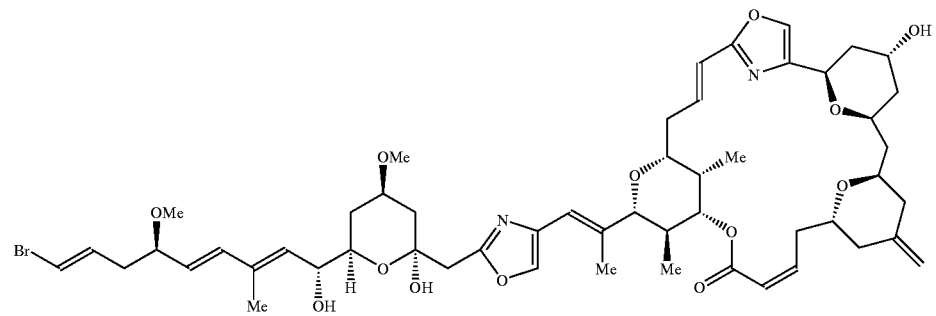 |
| 2 | 32-Methyl-phorboxolide A (C1–C32 analog) | 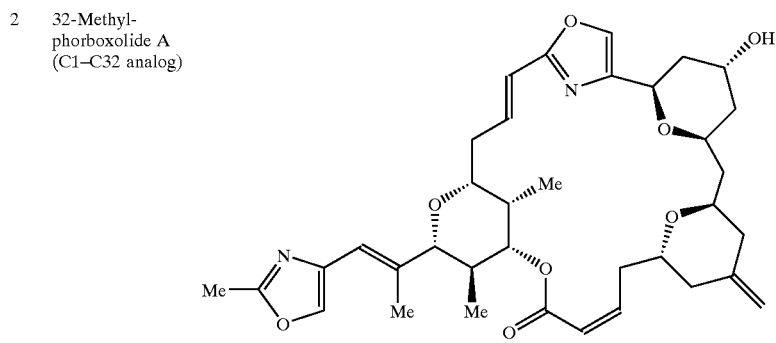 |

TABLE 2-continued
| Compound Number | Compound Name | Compound Structure |
|---|---|---|
| 3 | C1–C38 Phorboxazole A | 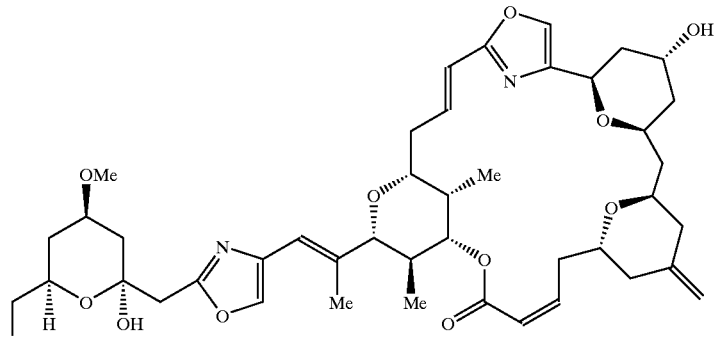 |
| 4 | 24-O-Acetyl-18-methyl-phorboxylate (C18–C46 analog) | 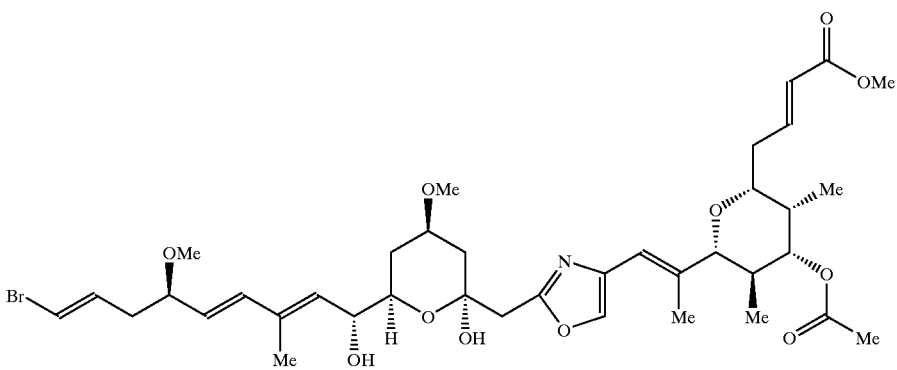 |
| 5 | 31-Methyl-phorboxylate (C31–C46 analog) | 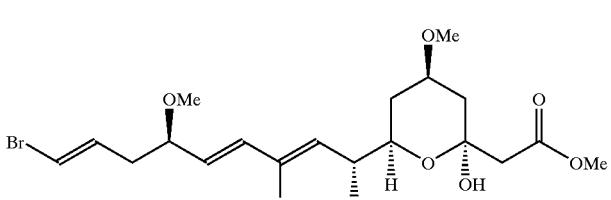 |
| 6 | 29-Phorboxamide A (hydrated analog) | 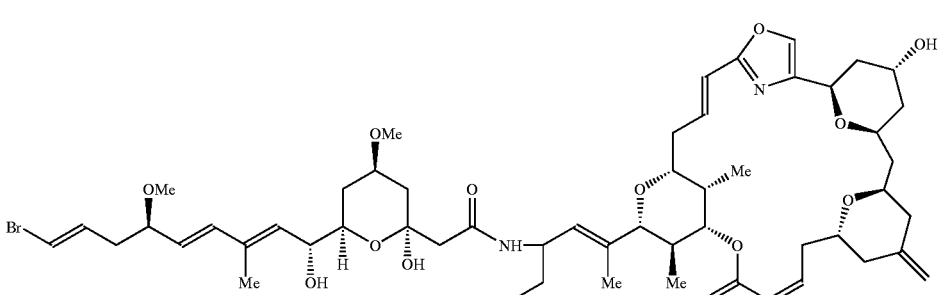 |

TABLE 2-continued

| Compound Number | Compound Name | Compound Structure |
|---|---|---|
| 7 | 45,46-Dehydrobromo-33-O-methyl-Phorboxazole A | 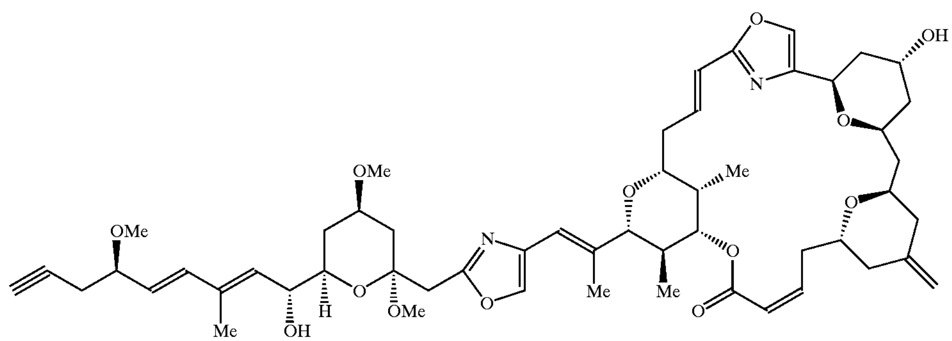 |
| 8 | 45,46-Dehydrobromo-Phorboxazole A | 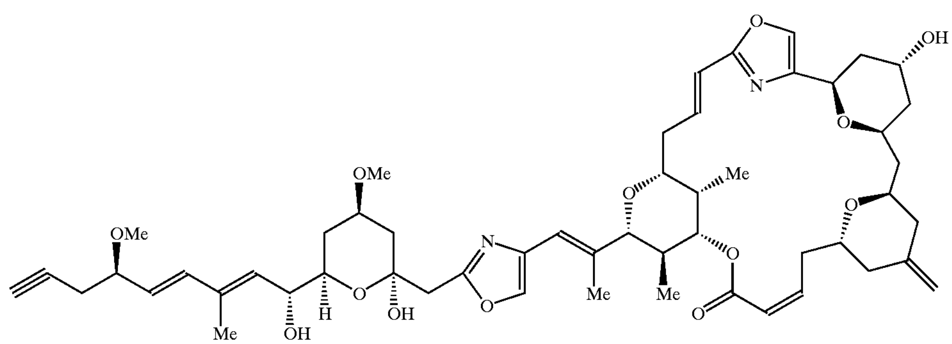 |
| 9 | 33-O-methyl-Phorboxazole A | 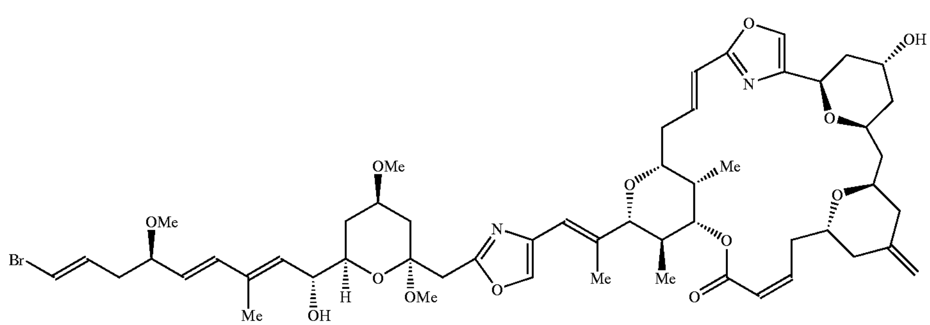 |
| 10 | 2,3-Dihydrophorboxazole A | 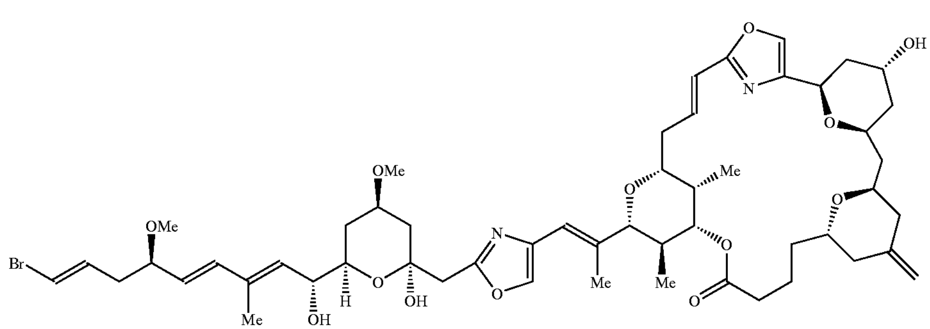 |

TABLE 3

IC$_{50}$ [MTT] (nM)

| Compound Number | Compound Name | NALM-6 (Leukemia) | BT-20 (Breast Cancer) | U373 (Brain Tumor) |
|---|---|---|---|---|
| 1 | Phorboxazole A | 1.7 | 3.4 | 6.7 |
| 2 | 32-Methyl-phorboxolide A (C1–C32 analog) | >2000 | >2000 | >2000 |
| 3 | C1–C38 Phorboxazole A | >2000 | >2000 | >2000 |
| 4 | 24-O-Acetyl-18-methyl-phorboxylate (C18–C46 analog) | >2000 | >2000 | >2000 |
| 5 | 31-Methyl-phorboxylate (C31–C46 analog) | >2000 | >2000 | >2000 |
| 6 | 29-Phorboxamide A (hydrated analog) | >2000 | >2000 | >2000 |
| 7 | 45, 46-Dehydrobromo-33-O-methyl-Phorboxazole A | >2000 | >2000 | >2000 |
| 8 | 45, 46-Dehydrobromo-Phorboxazole A | 4.8 | 12.6 | 27.4 |
| 9 | 33-O-methyl-Phorboxazole A | 5.2 | 11.3 | 29.2 |
| 10 | 2,3-dihydrophorboxazole A | >2000 | >2000 | >2000 |

In situ Detection of Apoptosis

The synthetic Phorboxazole A and the synthetic analogs were also assayed for apoptosis-inducing activity. Assay for apoptosis was performed by the in situ nick-end-labeling method using an ApopTag in situ detection kit (Oncor, Gaithersburg, Md.) according to the manufacturer's recommendations. Immunofluorescence was used to examine the morphologic features of human breast cancer cell line BT-20 (American Type Culture Collection Rockville, Md.) treated with the novel phorboxazole A derivatives of the present invention.

Cells were trypsinized from rapidly growing tissue culture flasks and seeded onto sterile 22 mm$^2$ coverslips in 6-well culture plates. Cells on coverslips were returned to the incubator for 24 hours prior to treatment. The phorboxazole A derivatives were added to the cells from a stock solution made in DMSO to a final concentration of 100 μM. Final DMSO concentration were kept at 0.1% in both test samples and controls. Cells were returned to a 37° C. incubation for 24 hours before further processing. At 24 hours, coverslips were fixed in −20° C. methanol for 15 minutes followed by a 15 minute incubation in phosphate buffered saline +0.1% Triton X-100 (PBS-Tx). Coverslips were then incubated with a monoclonal antibody against α-tubulin (Sigma Chemical Co., St. Louis, Mo.) at a dilution of 1:1000 for 40 minutes in a humidified chamber at 37° C. Coverslips were washed for 15 minutes in PBS-Tx followed by a 40 minute incubation with goat anti-mouse IgG antibody conjugated to FITC (Amersham Corp., Arlington Heights, Ill.). The coverslips were again rinsed in PBS-Tx and incubated with 5 μM TOTO-3 (Molecular Probes, Eugene, Oreg.) for 20 minutes to label the nuclear DNA. Coverslips were immediately inverted onto slides in Vectashield (Vector Labs, Burlingame) to prevent photobleaching, sealed with nail varnish and stored at 4° C.

Slides were examined using a Bio-Rad MRC-1024 Laser Scanning Confocal Microscope mounted on a Nikon Eclipse E800 upright microscope with high numerical aperture objectives. Digital data was processed using Lasersharp (Bio-Rad, Hercules, Calif.) and Adobe Photoshop software (Adobe Systems, Mountain View, Calif.) and printed on a Fuji Pictography thermal transfer printer (Fuji, Elmsford, N.Y.). The data showed apoptotic activity of synthetic Phorboxazole A and two of the synthesized analogs: 45,46-dehydrobromo-phorboxazole A and 33-O-methyl-phorboxazole A. None of the other synthetic analogs tested demonstrated ability to induce apoptosis.

Figure 2:
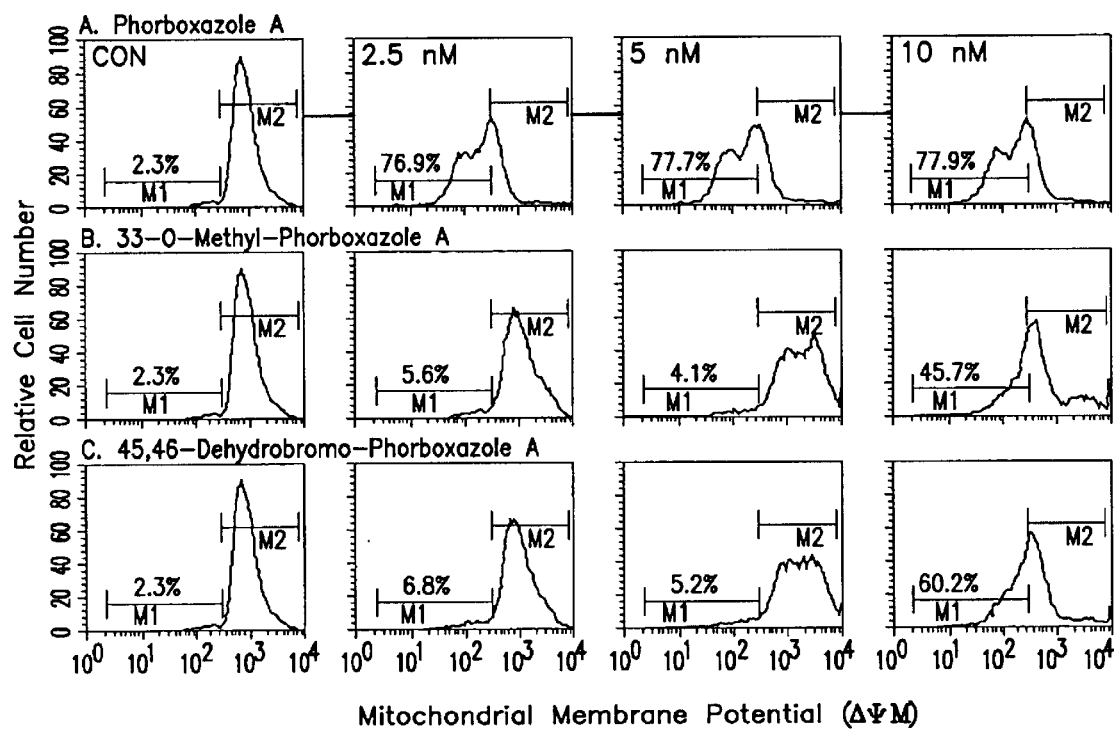
FIG. 2 are graphs showing the effect of synthetic phorboxazole A and phorboxazole A derivatives on the mitochondrial transmembrane potentials of leukemia NALM-6 cells.

In addition mitochondrial assay shows an increase in depolarized mitochondria as shown in FIG. 2. Cells were incubated with 2.5 nM, 5 nM or 10 nM of phorboxazole A, 33-O-methyl-phorboxazole A or 45,46-dehydrobromo-phorboxazole A for 72 hours, stained with DiIC1 (5) to assess the mitochondrial membrane potential (Δψm) and then analyzed with a cell sorter equipped with a HeNe laser. All three compounds caused a progressive increase in depolarized mitochondria in a dose dependent fashion.

Clonogenic Assays

The growth-inhibiting activity of the synthetic Phorboxazole A and the synthesized derivatives was tested in clonogenic assays. Cancer cells were treated with 1 nM, 10 nM, and 100 nM doses of synthetic Phorboxazole A or derivatives of phorboxazole A. Treated cells included U373 human glioblastoma cells, NALM-6, human B-lineage acute lymphoblastic leukemia cells, and BT-20 human breast cancer cells. The cancer cells were resuspended in clonogenic medium consisting of alpha-MEM supplemented with 0.9% methylcellulose, 30% fetal bovine serum, and 50 μM 2-mercaptoethanol. Cells were plated in duplicate Petri dishes at 100,000 cells/mL/dish and cultured in a humidified 5% $CO_2$ incubator for 7 days. Cancer cell colonies were enumerated on a grid using an inverted phase microscope of high optical resolution. Results were expressed as % inhibition of clonogenic cells at a particular concentration of the test agent using the formula:

% Inhibition=(1−Mean # of colonies [Test]/Mean # of colonies [Control])×100.

The effects of phorboxazole A derivatives on cologenic growth of these human cancer cells BT-20 are summarized below in Table 4, and demonstrate effective growth inhibiting activity of synthetic Phorboxazole A and two of the synthesized analogs: 45,46-dehydrobromo-phorboxazole A and 33-O-methyl-phorboxazole A.

TABLE 4

Inhibition of Clonogenic Growth of Human Cancer Cell Lines

| Human Cancer Cell Line | Treatment | | Mean Number Colonies/10$^4$ cells | Inhibition |
|---|---|---|---|---|
| NALM-6 B-lineage ALL | Vehicle (CON) | | 2046 (1736, 2356) | — |
| | Phorboxazole A | 1 nM | 270 (116, 424) | 86.8 |
| | | 10 nM | 0 (0, 0) | >99.9 |
| | | 100 nM | 0 (0, 0 | >99.9 |

TABLE 4-continued

Inhibition of Clonogenic Growth of Human Cancer Cell Lines

| Human Cancer Cell Line | Treatment | | Mean Number Colonies/$10^4$ cells | Inhibition) |
|---|---|---|---|---|
| | 45, 46 Dehydrobromo-Phorboxazole A | 1 nM | 2116 (1872, 2360) | 0.0 |
| | | 10 nM | 293 (200, 386) | 85.7 |
| | | 100 nM | 0 (0, 0) | >99.9 |
| | 33-O-Methyl-Phorboxazole A - | 1 nM | 1760 (1468, 2052) | 14.0 |
| | | 10 nM | 422 (316, 528) | 79.4 |
| | | 100 nM | 0 (0, 0) | >99.9 |
| BT-20 Breast Cancer | Vehicle (CON) | | 1524 (1256, 1792) | — |
| | Phorboxazole A - | 1 nM | 1070 (1028, 1112) | 29.8 |
| | | 10 nM | 0 (0, 0) | >99.9 |
| | | 100 nM | 0 (0, 0) | >99.9 |
| | 45, 46 Dehydrobromo-Phorboxazole A | 1 nM | 1540 (1492, 1588) | 0.0 |
| | | 10 nM | 1062 (1020, 1104) | 30.3 |
| | | 100 nM | 0 (0, 0) | >99.9 |
| | 33-O-Methyl-Phorboxazole A - | 1 nM | 1824 (1768, 1880) | 0.0 |
| | | 10 nM | 1430 (1264, 1596) | 6.2 |
| | | 100 nM | 0 (0, 0) | >99.9 |
| U373 Glioblastoma | Vehicle (CON) | | 656 (576, 736) | — |
| | Phorboxazole A - | 10 nM | 378 (364, 392) | 42.4 |
| | | 100 nM | 0 (0, 0) | >99.9 |
| | 45, 46 Dehydrobromo-Phorboxazole A | 10 nM | 586 (528, 644) | 10.7 |
| | | 100 nM | 144 (132, 156) | 78.1 |
| | 33 O-Methyl-Phorboxazole A | 10 nM | 578 (552, 604) | 11.9 |
| | | 100 nM | 0 (0, 0) | >99.8 |

Example 3

Phorboxazole Derivatives Inhibit Cancer Cell Adhesion

During the multistep process of tissue invasion, tumor cells initially adhere to the extracellular matrix (ECM) proteins via cell surface integrin receptors and then gain migratory capacity to enter the surrounding tissues. ECM proteins such as laminin, fibronectin, and type IV collagen are thought to play an important role in tumor cell attachment and migration. Laminin, fibronectin and collagen have been found in the basal lamina of blood vessels and in the glial limitans externa in the brain that promote the adhesion and invasion of tumor cells in situ (Carbonetto, S., 1984, *Trends Neurosci.*, 7:382–387; Rutka, J. T., Apodaca, G., Stern, R., *J. Neurosurg.*, 69:155–170; Venstrom, K. A. and Reichard, L. F., 1993, *FASEB J.*, 7:996–1003).

The effects of these ECM proteins on integrin-mediated glioblastoma and breast cancer cell adhesion was examined using human glioblastoma cell line U373 and two breast cancer cell lines, BT-20 and MDA-MB-231, in the presence of synthetic Phorboxazole A and synthetic analogs thereof.

Human brain tumor cell lines U-373 MG and breast cancer cell lines BT-20 and MDA-MB-231 were obtained from American Type Culture Collection (ATCC, Rockville, Md.) and maintained in liquid culture using DMEM supplemented with 10% fetal bovine serum and antibiotics. Fibroblast conditioned medium was used as a source of chemoattractant in vitro invasion assays. Conditioned medium was prepared as described in the literature (Albini et.al., 1987, *Cancer Res.*, 47:3239–3245).

For the preparation of this conditioned medium, NIH/3T3 embryonic fibroblasts (ATCC accession number CRL-1658) were grown to 80% confluency in DMEM medium supplemented with 10% FBS and cultured for 24 hours in serum-free medium containing 0.5 $\mu$g/ml bovine serum albumin The culture supernatants were collected, centrifuged at 1000×g for 15 minutes to remove cellular debris and used as conditioned medium.

In vitro adhesion assays were performed to (a) study the baseline adhesive properties of various breast cancer and glioblastoma cell lines and (b) evaluate the effects of phorboxazole A derivatives on the adhesive properties of breast cancer and glioblastoma cells. The plates for the adhesion assays were precoated with the extracellular matrix proteins laminin, fibronectin, or type IV collagen (each at a final concentration of 1 $\mu$g/ml in PBS) overnight at 4° C. and dried. On the day of the experiment, the wells were rehydrated and blocked with 10% bovine serum albumin in PBS for 1 hour at room temperature and used for the adhesion assays, as described below.

The effects of synthetic phorboxazole A and specific derivatives on adhesion of breast cancer and glioblastoma cells was studied. Exponentially growing cells in DMEM were incubated with phorboxazole compounds or genistein as a control at concentrations ranging from 0.1 $\mu$M to 1 $\mu$M for 24 hours in a humidified 5% $CO_2$ atmosphere. DMSO (0.1%) was included as a vehicle control. After treatment, cells were detached from the flasks with 0.05% trypsin (Life Technologies) resuspended in DMEM, incubated at 37° C. for 2 hours to allow them to recover from the trypsinization stress and examined for their ability to adhere to plates precoated with ECM proteins.

In adhesion assays, cells were centrifuged, washed twice with serum-free DMEM, counted and resuspended in serum-free DMEM to a final concentration of $2.5 \times 10^5$ cells/ml. One hundred $\mu$l of the cell suspension containing $2.5 \times 10^4$ cells were added to each well and cells were allowed to adhere for 1 hour at 37° C. in a humidified 5% $CO_2$ atmosphere. The adherent fraction was quantitated using MTT (3-[4,5-dimethylthiazol-2-yl]-2,5-diphenyltetrazolium bromide) assays. In brief, after washing the wells, 10 $\mu$l of MTT (0.5 mg/ml final concentration) (Boehringer Mannheim Corp., Indianapolis, Ind.) was added to each well and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbance of each well was measured in a microplate reader (Labsystems) at 540 nm and a reference wavelength of 690 nm.

To translate the $OD_{540}$ values into the number of cells in each well, the $OD_{540}$ values were compared to those on standard $OD_{540}$-versus-cell number curves generated for each cell line. The adherent fractions of cells treated with phorboxazole A derivatives were compared to those of DMSO-treated control cells and the percent inhibition of adhesion was determined using the formula:

$$\% \text{ Inhibition} = 100 * \frac{1 - \text{Adherent Fraction of Drug Treated Cells}}{\text{Adherent Fraction of Control Cells}}$$

Each treatment condition was evaluated in duplicate in 3 independent experiments. The $IC_{50}$ values were calculated by non-linear regression analysis. Synthetic phorboxazole A and novel phorboxazole derivatives inhibited the adhesion of U373, BT-20 and MDA-MB-231 cells to laminin-, fibronectin-, and collagen-coated plates in a dose-dependent fashion. Surprisingly, the most active analogs for inhibiting cell adhesion were not cytotoxic. The active compounds were: synthetic Phorboxazole A; 29-phorboxamide A; 31-methyl-phorboxylate; and 18-methyl-phorboxylate (see FIG. 3).

Example 4

Inhibition of Cancer Cell Invasion

The in vitro invasiveness of human brain tumor cell lines U-373 MG and breast cancer cell lines BT-20 and MDA-MB-231 cells was assayed using a previously published method which employs Matrigel™-coated Costar 24-well transwell cell culture chambers ("Boyden chambers") with 8.0-μm-pore polycarbonate filter inserts (Albini,et.al, 1987, Cancer Res., 47:3239–3245). The chamber filters were coated with 50 μg/ml of Matrigel™ matrix, incubated overnight at room temperature under a laminar flow hood and stored at 4° C. Matrigel™ matrix is made up of several components of the extracellular matrix (ECM), including collagen, laminin and proteo-glycans. The cancer cells were incubated with 500, 250, 125, 62.5, and 31.2 nM concentrations of the synthetic Phorboxazole compounds for 72 hours.

On the day of the experiment, the coated inserts were rehydrated with 0.5 ml serum-free DMEM containing 0.1% bovine serum albumin for 1–2 hours. The treated cells were trypsinized, washed twice with serum-free DMEM containing BSA, counted and resuspended at $1 \times 10^5$ cells/ml. A 0.5 ml cell suspension containing $5 \times 10^4$ cells in a serum-free DMEM was added to the Matrigel™-coated and rehydrated filter inserts. A volume of 750 μl of NIH fibroblast conditioned medium was placed as a chemoattractant in 24-well plates and the inserts were placed in wells and incubated at 37° C. for 48 hours.

After the incubation period, the filter inserts were removed, the medium was decanted off and the cells on the top side of the filter that did not migrate were scraped off with a cotton-tipped applicator. The invasive cells that migrated to the lower side of the filter were fixed, stained with Hema-3 solutions and counted under microscope. Five to 10 random fields per filter were counted to determine the mean (±SE) values for the invasive fraction. The invasive fractions of cells treated with phorboxazole A derivatives were compared to those of DMSO treated control cells and the percent inhibition of invasiveness was determined using the formula:

$$\% \text{ Inhibition} = 100 \left[ \frac{1 - \text{Adherent Fraction of Drug Treated Cells}}{\text{Adherent Fraction of Control Cells}} \right]$$

Each treatment condition was evaluated in duplicate in 3 independent experiments. $IC_{50}$ values were calculated by non-linear regression analysis using Graphpad Prisin Software Version 2.0 (Graphpad Software Inc., San Diego, Calif.).

U373 glioblastoma as well as BT-20 and MDA-MB-231 breast cancer cells were highly invasive in MatrigelT-coated Boyden chambers. The inhibition by the synthetic phorboxazole compounds of the inventions is shown below in Table 5.

TABLE 5

Inhibition of glioblastoma cell invasion through Matirigel ™

| compound | $IC_{50}$ (nM) |
|---|---|
| Phorboxazole A | <31.2 |
| 29-phorboxamide | <125 |
| 18-methyl-phorboxamide | 151.5 |
| 31-methyl-phorboxylate | 421.8 |

Example 5

Phorboxazole A Derivatives Inhibit Cancer Cell Migration from Spheroids

U373 glioblastoma spheroids of 200 to 400 micrometers in diameter were treated with synthetic Phorboxazole A, 33-O-Methyl-phorboxazole A, and 45,46-dehydrobromo-phorboxazole A in 0.1% DMSO at varied concentrations. Cells were incubated with the inhibitor or with control DMSO in the absence of inhibitor compound for two hours, and then transferred to fibronectin-coated coverslips. The spheroids were then incubated in DMEM containing WHI-P154 at 37° C. for 48 hours.

Treatment of glioblastoma spheroids with 33-O-Methyl-phorboxazole A or 45,46-dehydrobromo-phorboxazole A significantly inhibited cell migration from the spheroid as compared with the untreated control and in a dose-dependent manner.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

In addition, multi-cellular U373 glioblastoma spheroids of 200–400 μm diameter were incubated with 500 nM, 250 nM, 125 nM, 62.5 nM and 31.35 nM phorboxazoleA, 29-phorboxamide A, 18-methyl phorboxylate and 31-methyl phorboxylate in 0.1% DMSO or 0.1% DMSO alone for 2 hours and transferred to fibronectin-coated coverslips. The spheroids were then incubated in MEM containing respective compounds and cultured for 48 hours at 37° C. At the end of incubation, the spheroids were fixed and stained with Hema-3 solutions. The distance of migrated cells from spheroids was measured using a mircoscope and micrometer.

Numerous publications have been cited in the text of this specification. Each such publication is expressly incorporated by reference for all purposes, as if fully set forth.

What is claimed is:

1. A composition comprising an effective therapeutic amount of:

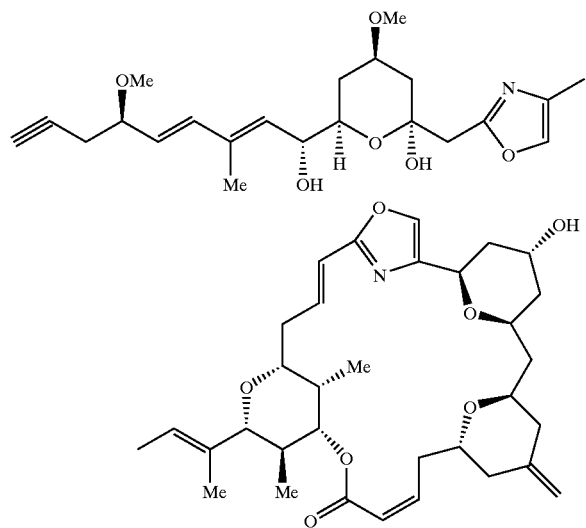

and a pharmaceutically acceptable carrier.

2. The composition of claim 1, wherein said compound is formulated as a prodrug.

3. A method for inducing apoptosis of leukemia cells, breast cancer cells, prostate cancer cells, or brain cancer cells, said method comprising contacting said cells with an effective apoptosis-inducing amount of the compound of claim 1.

4. A method for inhibiting leukemia cell, breast cancer cell, prostate cancer cell, or brain cancer cell division, said method comprising contacting said cells with an effective inhibitory dose of the compound of claim 1.

5. A method for treating leukemia, breast cancer, prostate cancer, or brain cancer in a mammal comprising administering to said mammal an effective therapeutic dose of a compound of claim 1.

6. A composition comprising a therapeutically effective dose of one or more of: 29-phorboxamide A, 31-methyl-phorboxylate, and 18-methyl-phorboxylate; and a pharmaceutically acceptable carrier.

7. A method for preventing adhesion or migration of leukemia cells, breast cancer cells, prostate cancer cells, or brain cancer cells, said method comprising contacting said cells with the composition of claim 6.

8. A method for treating leukemia, breast cancer, prostate cancer, or brain cancer in a mammal comprising administering to said mammal an effective therapeutic amount of the composition according to claim 6.

9. A method for inducing apoptosis of leukemia cells, breast cancer cells, prostate cancer cells, or brain cancer cells, said method comprising contacting said cells with an effective apoptosis-inducing amount of the composition of claim 6.

10. A method for inhibiting division of leukemia cells, breast cancer cells, prostate cancer cells, or brain cancer cells, said method comprising contacting said cells with an effective inhibitory dose of the composition of claim 6.

11. A method for treating leukemia, breast cancer, prostate cancer, or brain cancer in a mammal comprising administering to said mammal an effective therapeutic dose of the composition of claim 6.

* * * * *

UNITED STATES PATENT AND TRADEMARK OFFICE
CERTIFICATE OF CORRECTION

| | | |
|---|---|---|
| PATENT NO. | : 6,797,721 B2 | Page 1 of 1 |
| APPLICATION NO. | : 10/146601 | |
| DATED | : September 28, 2004 | |
| INVENTOR(S) | : Fatih M. Uckun | |

It is certified that error appears in the above-identified patent and that said Letters Patent is hereby corrected as shown below:

Col. 1
Please insert the following text prior to Background of Invention:

Government Interests
FEDERALLY SPONSORED RESEARCH
The United States Government may have certain rights in this invention pursuant to National Institutes of Health Grant No. 5R01-GM55756-03.

Signed and Sealed this

Twentieth Day of March, 2007

JON W. DUDAS
*Director of the United States Patent and Trademark Office*